US011870035B2

(12) United States Patent
Tsuji et al.

(10) Patent No.: US 11,870,035 B2
(45) Date of Patent: Jan. 9, 2024

(54) NON-AQUEOUS ELECTROLYTE SECONDARY CELL

(71) Applicant: Panasonic Intellectual Property Management Co., Ltd., Osaka (JP)

(72) Inventors: Tomoki Tsuji, Osaka (JP); Yuanlong Zhong, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 809 days.

(21) Appl. No.: 16/640,293

(22) PCT Filed: Jul. 19, 2018

(86) PCT No.: PCT/JP2018/027024
§ 371 (c)(1),
(2) Date: Feb. 19, 2020

(87) PCT Pub. No.: WO2019/044238
PCT Pub. Date: Mar. 7, 2019

(65) Prior Publication Data
US 2021/0083325 A1 Mar. 18, 2021

(30) Foreign Application Priority Data
Aug. 30, 2017 (JP) ................. 2017-165274

(51) Int. Cl.
*H01M 10/0567* (2010.01)
*C07D 319/12* (2006.01)
(Continued)

(52) U.S. Cl.
CPC ...... *H01M 10/0567* (2013.01); *C07D 319/12* (2013.01); *H01M 4/505* (2013.01);
(Continued)

(58) Field of Classification Search
None
See application file for complete search history.

(56) References Cited

U.S. PATENT DOCUMENTS

2007/0042267 A1* 2/2007 Kim ................. H01M 10/0569
429/231.95
2008/0213670 A1 9/2008 Okada et al.
(Continued)

FOREIGN PATENT DOCUMENTS

JP 2002-8717 A 1/2002
JP 2005-78866 A 3/2005
(Continued)

OTHER PUBLICATIONS

International Search Report dated Oct. 23, 2018, issued in counterpart application No. PCT/JP2018/027024 (2 pages).
(Continued)

*Primary Examiner* — Robert S Carrico
(74) *Attorney, Agent, or Firm* — WHDA, LLP

(57) ABSTRACT

A non-aqueous electrolyte secondary cell provided with a positive electrode, a negative electrode, and a non-aqueous electrolyte. The positive electrode has a positive electrode active material that contains composite oxide particles which include Ni, Co, Li, and at least one of Mn and Al, and in which the proportion of Ni in relation to the total number of moles of metal elements excluding Li is at least 80 mol %. In the composite oxide particles, the ratio (B/A) of the post-particle-compression-test BET specific surface area (B) with respect to the pre-particle-compression-test BET specific surface area (A) is 1.0-3.0. The non-aqueous electrolyte contains a non-aqueous solvent and a cyclic carboxylic anhydride such as diglycolic anhydride.

8 Claims, 1 Drawing Sheet

(51) Int. Cl.
    *H01M 4/505*     (2010.01)
    *H01M 4/525*     (2010.01)
    *H01M 4/62*     (2006.01)
    *H01M 10/052*     (2010.01)
    *H01M 4/02*     (2006.01)

(52) U.S. Cl.
    CPC ............. *H01M 4/525* (2013.01); *H01M 4/62* (2013.01); *H01M 10/052* (2013.01); *H01M 2004/028* (2013.01); *H01M 2300/0025* (2013.01)

(56) References Cited

U.S. PATENT DOCUMENTS

| | | | |
|---|---|---|---|
| 2009/0253045 A1 | 10/2009 | Kotato et al. | |
| 2009/0272940 A1* | 11/2009 | Kikuya | C01G 51/42 252/182.1 |
| 2010/0183926 A1 | 7/2010 | Kim et al. | |
| 2015/0221943 A1* | 8/2015 | Nishioka | H01M 4/505 429/223 |
| 2016/0248090 A1 | 8/2016 | Maeda et al. | |
| 2017/0214087 A1 | 7/2017 | Yoshida et al. | |
| 2019/0198870 A1* | 6/2019 | Watano | H01M 4/587 |

FOREIGN PATENT DOCUMENTS

| | | |
|---|---|---|
| JP | 2008-251527 A | 10/2008 |
| JP | 2010-170991 A | 8/2010 |
| JP | 2013-182807 A | 9/2013 |
| JP | 2013-239307 A | 11/2013 |
| JP | 2016-157677 A | 9/2016 |
| JP | 2017-112010 A | 6/2017 |
| WO | 2015/156400 A1 | 10/2015 |
| WO | 2015/199063 A1 | 12/2015 |
| WO | 2017/169129 A1 | 10/2017 |
| WO | 2018/116941 A1 | 6/2018 |

OTHER PUBLICATIONS

English Translation of Search Report dated Dec. 17, 2021, issued in counterpart CN Application No. 201880053590.0. (4 pages).

* cited by examiner

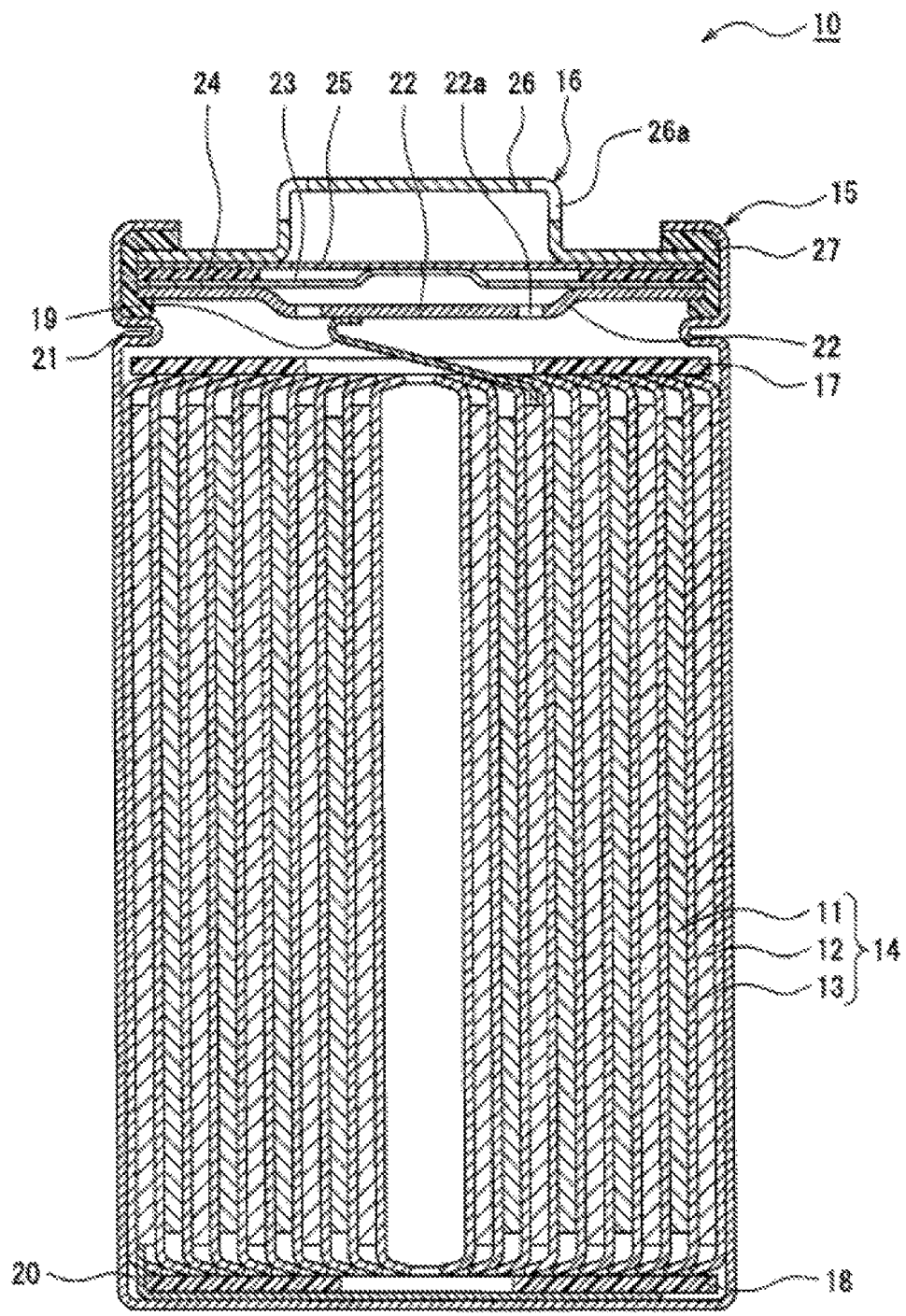

NON-AQUEOUS ELECTROLYTE SECONDARY CELL

TECHNICAL FIELD

The present invention relates to technology of a non-aqueous electrolyte secondary battery.

BACKGROUND ART

Non-aqueous electrolyte secondary batteries which comprise a positive electrode, a negative electrode and a non-aqueous electrolyte and are charged and discharge by transferring lithium ions between the positive electrode and the negative electrode have been used widely as secondary batteries having high outputs and high energy densities in recent years.

For example, Patent Literature 1 proposes a secondary battery, comprising a positive electrode including a positive electrode active material, a negative electrode including an negative electrode active material and an electrolytic solution, wherein the positive electrode and/or the negative electrode has an organic moiety comprising resin and an inorganic moiety comprising silica and includes a binding agent containing an organic-inorganic hybrid material which binds the positive electrode active material and/or the negative electrode active material, and the electrolytic solution includes a fluorine-containing cyclic carbonate containing at least one fluorine atom.

CITATION LIST

Patent Literature

PATENT LITERATURE 1: Japanese Unexamined Patent Application Publication No. 2013-182807

SUMMARY

Incidentally, although complex oxide particles, including Ni, Co and Li and including at least either of Mn and Al, wherein the ratio of Ni to the total number of moles of the metallic elements except Li is 80 mol % or more are an excellent material as a positive electrode active material, the complex oxide particles have a problem that the capacity deterioration rate after the storage of the battery at high temperature increases. The capacity deterioration rate after storage at high temperature is a value indicating the deterioration degree of the battery capacity of a non-aqueous electrolyte secondary battery (capacity after storage) when charge and discharge are performed again at room temperature (for example, 25° C.) after the non-aqueous electrolyte secondary battery in the charging state is stored at high temperature (for example, 40° C. or more) for predetermined days based on the battery capacity of the non-aqueous electrolyte secondary battery when charge and discharge are performed at room temperature (for example, 25° C.) (initial capacity).

Then, an object of the present disclosure is to provide a non-aqueous electrolyte secondary battery which enables suppressing an increase in the capacity deterioration rate after storage at high temperature even though a positive electrode active material including complex oxide particles, including Ni, Co and Li and including at least either of Mn and Al, wherein the ratio of Ni to the total number of moles of the metallic elements except Li is 80 mol % or more is used.

A non-aqueous electrolyte secondary battery according to one aspect of the present disclosure comprises: a positive electrode; a negative electrode; and a non-aqueous electrolyte, the positive electrode has a positive electrode active material including complex oxide particles, including Ni, Co and Li and including at least either of Mn and Al, wherein the ratio of Ni to the total number of moles of the metallic elements except Li is 80 mol % or more, the complex oxide particles have a ratio of the BET specific surface area after a particle compression test (B) to the BET specific surface area before the particle compression test (A) (B/A) of 1.0 or more and 3.0 or less, and the non-aqueous electrolyte includes a cyclic carboxylic anhydride represented by the following formula (1) and a non-aqueous solvent.

[Formula 1]

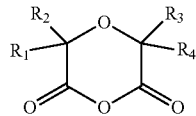

In the formula, $R_1$ to $R_4$ each independently represent H, an alkyl group, an alkene group or an aryl group.

According to a non-aqueous electrolyte secondary battery according to one aspect of the present disclosure, the suppression of an increase in the capacity deterioration rate after storage at high temperature is enabled even though a positive electrode active material including complex oxide particles, including Ni, Co and Li and including at least either of Mn and Al, wherein the ratio of Ni to the total number of moles of the metallic elements except Li is 80 mol % or more is used.

BRIEF DESCRIPTION OF DRAWINGS

FIG. 1 is a sectional view of a non-aqueous electrolyte secondary battery which is one example of an embodiment.

DESCRIPTION OF EMBODIMENTS

Surface deterioration such as the production of a compound of nickel and oxygen on the surfaces of complex oxide particles, including Ni, Co and Li and including at least either of Mn and Al, wherein the ratio of Ni to the total number of moles of the metallic elements except Li is 80 mol % or more may occur when a non-aqueous electrolyte secondary battery is stored at high temperature (for example, 40° C. or more). It is considered that the capacity deterioration rate after the storage of the non-aqueous electrolyte secondary battery at high temperature increases partly due to such surface deterioration of the complex oxide particles.

Then, the present inventors have examined earnestly, consequently found that the surface deterioration of complex oxide particles (the production of a compound of nickel and oxygen) is suppressed by the combination of the complex oxide particles having a specific BET surface area and a non-aqueous electrolyte including a cyclic carboxylic anhydride also when a non-aqueous electrolyte secondary battery is stored at high temperature, and considered the non-aqueous electrolyte secondary battery of an aspect described below.

A non-aqueous electrolyte secondary battery according to one aspect of the present disclosure comprises: a positive electrode; a negative electrode; and a non-aqueous electrolyte, the positive electrode has a positive electrode active material including complex oxide particles, including Ni, Co and Li and including at least either of Mn and Al, wherein the ratio of Ni to the total number of moles of the metallic elements except Li is 80 mol % or more, the complex oxide particles have a ratio of the BET specific surface area after a particle compression test (B) to the BET specific surface area before the particle compression test (A) (B/A) of 1.0 or more and 3.0 or less, and the non-aqueous electrolyte includes a cyclic carboxylic anhydride represented by the following formula (1) and a non-aqueous solvent.

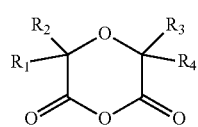

[Formula 1]

In the formula, $R_1$ to $R_4$ each independently represent H, an alkyl group, an alkene group or an aryl group.

The BET specific surface area before the particle compression test (A) in the above-mentioned complex oxide particles is the BET specific surface area of complex oxide particles taken out by disassembling the non-aqueous electrolyte secondary battery or the complex oxide particles to be used for the non-aqueous electrolyte secondary battery. The BET specific surface area is a value measured in accordance with a BET method described in JIS R1626 (nitrogen adsorption method). The BET specific surface area after the particle compression test (B) in the above-mentioned complex oxide particles is the BET specific surface area of the complex oxide particles after the complex oxide particles taken out by disassembling the non-aqueous electrolyte secondary battery or the complex oxide particles to be used for the non-aqueous electrolyte secondary battery are subjected to a compression test under the following conditions. The particle compression test mentioned herein is a test in which positive electrode mixture slurry including the above-mentioned complex oxide particles, a conductive agent, a binding agent and the like is applied to a positive electrode current collector and dried to form a positive electrode active material layer, and the positive electrode mixture layer is rolled until the mixture density is 3.4 g/cc, and the complex oxide particles are compressed.

Here, the ratio of the BET specific surface area after a particle compression test (B) to the BET specific surface area before the particle compression test (A) (B/A) is 1.0 or more and 3.0 or less, and it is shown thereby that almost all the surfaces of the primary particles are exposed. For example, unaggregated particles or the like satisfies the above-mentioned range. The unaggregated state include not only a state in which particles are completely separated into individual primary particles but also a state in which around several (for example, 2 to 15) primary particles are gathered. For example, even though the particles are aggregated particles in which around tens of primary particles are aggregated, particles or the like in which holes in the aggregated particles are very large satisfy the above-mentioned range. It is considered that when the complex oxide particles are unaggregated particles or aggregated particles in which around tens of primary particles are aggregated, and holes in the aggregated particles are very large, the non-aqueous electrolyte contacts with almost all the surfaces of the primary particles, and a coating derived from the cyclic carboxylic anhydride in the non-aqueous electrolyte is therefore formed on almost all the surfaces of the primary particles. Since the coating of derived from the cyclic carboxylic anhydride is hardly decomposed by storing the battery at high temperature, and covers the surfaces of the particles, the surface deterioration of the complex oxide particles (production of the compound of nickel and oxygen) is suppressed, and an increase in the capacity deterioration rate is suppressed.

Meanwhile, the ratio of the BET specific surface area after a particle compression test (B) to the BET specific surface area before the particle compression test (A) (B/A) is more than 3.0, and it is shown thereby that almost no surfaces of the primary particles are exposed. For example, the ratio of aggregated particles wherein hundreds of primary particles or more are aggregated, and holes in the aggregated particles are very small, or the like is in the above-mentioned range. When the complex oxide particles are aggregated particles in which hundreds of primary particles or more are aggregated, and holes in the aggregated particles are very small, the non-aqueous electrolyte hardly infiltrates into the aggregated particles, and the coating derived from the cyclic carboxylic anhydride in the non-aqueous electrolyte is therefore hardly formed on the surfaces of the primary particles in the aggregated particles. Therefore, when the battery is stored at high temperature, the surface deterioration in which the compound of nickel and oxygen is produced occurs preferentially on the surfaces of the primary particles in the aggregated particles, and an increase in the capacity deterioration rate is therefore promoted.

An example of embodiments will be described in detail hereinafter. The drawing referred to in the explanation of embodiments is described schematically, and the dimensional ratios and the like of components depicted in the drawing may be different from those of actual articles.

FIG. 1 is a sectional view of a non-aqueous electrolyte secondary battery which is an example of embodiments. A non-aqueous electrolyte secondary battery 10 shown in FIG. 1 comprises: a wound electrode assembly 14 formed by winding a positive electrode 11 and a negative electrode 12 through a separator 13; a non-aqueous electrolyte; insulating plates 17 and 18 disposed above and below the electrode assembly 14, respectively; and a battery case storing the above-mentioned members. The battery case is constituted by a bottomed cylindrical case body 15 and a sealing assembly 16. An electrode assembly in another shape such as a layered electrode assembly in which a positive electrode and a negative electrode through a separator are layered by turns may be applied instead of the wound electrode assembly 14. Examples of the battery case include metal cases such as cylindrical shapes, square shapes, coin shapes and button shapes; and cases made of resins (laminated batteries) formed by laminating resin sheets.

The case body 15 is, for example, a bottomed cylindrical metal container. A gasket 27 is provided between the case body 15 and the sealing assembly 16, and the sealability in the battery case is secured. The case body 15 preferably has a projecting portion 21 which is formed, for example, by pressing a side portion from outside and supports the sealing assembly 16. The projecting portion 21 is preferably formed in a ring shape along the circumferential direction of the case body 15, and supports the sealing assembly 16 on its upper surface.

The sealing assembly 16 has a filter 22 in which the openings of the filter 22a are formed, and vent members disposed on the filter 22. The vent members (a lower vent member 23, an upper vent member 25 and the like) cover the openings of the filter 22a of the filter 22. When the internal pressure of the battery increases by heat generation due to an internal short circuit or the like, the vent members rupture. In the present embodiment, the lower vent member 23 and the upper vent member 25 are provided as the vent members, and an insulating member 24 disposed between the lower vent member 23 and the upper vent member 25, and a cap 26 having cap openings 26a are further provided. Members constituting the sealing assembly 16 have, for example, disk shapes or ring shapes, and the members except the insulating member 24 are electrically connected with each other. The filter 22 and the lower vent member 23 are specifically mutually united at the peripheries. The upper vent member 25 and the cap 26 are mutually united at the peripheries. The lower vent member 23 and the upper vent member 25 are connected with each other at the centers, and the insulating member 24 is between the peripheries. When the internal pressure increases by heat generation due to an internal short circuit or the like, for example, the thin portion of the lower vent member 23 ruptures. The upper vent member 25 swells to the cap 26 side thereby, and are separated from the lower vent member 23. The electrical connection between both is cut off thereby.

In the non-aqueous electrolyte secondary battery 10 shown in FIG. 1, a positive electrode lead 19 attached to the positive electrode 11 extends to the sealing assembly 16 side through the through hole of the insulating plate 17, and a negative electrode lead 20 attached to the negative electrode 12 extends to the bottom side of the case body 15 through the outside of the insulating plate 18. For example, the positive electrode lead 19 is connected with the bottom surface of the filter 22, which is the bottom plate of the sealing assembly 16, by welding or the like. The cap 26, which is the top plate of the sealing assembly 16 electrically connected with the filter 22, is a positive electrode terminal. The negative electrode lead 20 is connected with the bottom of the inside of the case body 15 by welding or the like. The case body 15 is a negative electrode terminal.

The positive electrode, the negative electrode, the non-aqueous electrolyte and the separator will be described in detail hereinafter.

[Positive Electrode]

The positive electrode 11 comprises, for example, a positive electrode current collector and a positive electrode active material layer formed on the positive electrode current collector. Foil of a metal such as aluminum which is stable in the potential range of the positive electrode, a film wherein the metal is disposed on the outer layer, or the like can be used for the positive electrode current collector.

The positive electrode active material layer includes a positive electrode active material. The positive electrode active material layer preferably include a binding agent in that positive electrode active materials can be bound to secure the mechanical strength of the positive electrode active material layer, or the binding property between the positive electrode active material layer and the positive electrode current collector can be increased. The positive electrode active material layer preferably includes a conductive agent in that the conductivity of the layer can be improved.

The positive electrode active material includes complex oxide particles, including Ni, Co and Li and including at least either of Mn and Al, wherein the ratio of Ni to the total number of moles of the metallic elements except Li is 80 mol % or more. This complex oxide particles will be called complex oxide particles with a high content of Ni hereinafter.

The complex oxide particles with a high content of Ni are preferably, for example, complex oxide particles represented by the general formula $Li_xNi_{1-y-z}Co_yM_zO_2$ wherein $0.9 \leq x \leq 1.2$, $0 < y+z \leq 0.2$, and M is at least one metallic element of the group consisting of Al and Mn. Although the rate of Ni of the complex oxide particles with a high content of Ni may be 80 mol % or more as mentioned above, the rate is preferably 80 mol % or more and 95 mol % or less (in the case of the above-mentioned general formula, it is preferable that $0.05 \leq y+z \leq 0.2$), for example, from the viewpoint that the capacity of the non-aqueous electrolyte secondary battery can be increased. The complex oxide particles with a high content of Ni may include metallic elements other than Li, Ni, Co, Al and Mn, and examples of the elements include Na, Mg, Sc, Y, Fe, Cu, Zn, Cr, Pb, Sb and B.

Although the complex oxide particles with a high content of Ni may have a ratio of the BET specific surface area after a particle compression test (B) to the BET specific surface area before the particle compression test (A) (B/A) of 1.0 or more and 3.0 or less, the above-mentioned ratio (B/A) is preferably 1.0 or more and 2.0 or less in that the capacity deterioration rate when the battery is stored at high temperature is further suppressed.

The complex oxide particles with a high content of Ni are preferably unaggregated particles. That is, the complex oxide particles with a high content of Ni preferably exist in a state in which particles are completely separated into individual primary particles or a state in which around several (for example, 2 to 15) primary particles are gathered in the positive electrode active material layer. The coating derived from the cyclic carboxylic anhydride in the non-aqueous electrolyte is formed in almost all the surfaces of the complex oxide particles with a high content of Ni thereby, the surface deterioration in which the compound of nickel and oxygen is produced is easily suppressed, and an increase in the capacity deterioration rate is therefore suppressed.

The unaggregated state of the complex oxide particles with a high content of Ni is observed by sectional SEM images through a scanning electron microscope (SEM). For example, the positive electrode 11 is embedded into a resin, a section of the positive electrode is prepared by cross section polisher (CP) processing or the like, and the section of the positive electrode active material layer in this section is photographed through the SEM. Alternatively, powder of the lithium transition metal oxide is embedded into a resin, a particle section of the lithium transition metal oxide is prepared by cross section polisher (CP) processing or the like, and this section is photographed through the SEM. Particles wherein the particle sizes confirmed in a sectional SEM image are in the error range of 10% or less from the volume average particle size are first selected, and the primary particle sizes are confirmed. Each primary particle and each aggregated particle are considered as true spheres, and the quantification of a state in which primary particles are gathered is calculated by the ratio of the volume of the primary particle to the volume estimated from the volume average particle size.

The average particle size (D50) of the complex oxide particles with a high content of Ni is preferably, for example, 2 μm or more and 20 μm or less. When the average particle size (D50) is less than 2 μm and more than 20 μm, the packing density in the positive electrode active material layer may decrease, and the capacity of the non-aqueous electrolyte secondary battery may decrease as compared with when the above-mentioned range is satisfied. Particles which are objects of the measurement of the average particle size include particles in not only a state in which particles are completely separated into individual primary particles but also a state in which around several (for example, 2 to 15) primary particles are gathered to be one particle. The average particle size (D50) of the positive electrode active material can be measured by laser diffractometry, for example, using MT3000II manufactured by MicrotracBEL Corp.

The compressive strength of the complex oxide particles with a high content of Ni is preferably 250 MPa or more, and more preferably 350 MPa or more. When the compressive strength of the complex oxide particles with a high content of Ni satisfies the above-mentioned range, the breakage of the particles due to charge and discharge is suppressed as compared with when the compressive strength does not satisfy the above-mentioned range. Since the breakage of the particles produces new surfaces on the particles, and leads to the occurrence of the surface deterioration in which the compound of nickel and oxygen is produced, the compressive strength of the complex oxide particles with a high content of Ni satisfies the above-mentioned range, and the suppression of an increase in the capacity deterioration rate after storage at high temperature is enabled thereby. Although the upper limit value of the compressive strength of the complex oxide particles with a high content of Ni is not particularly limited, the upper limit value is preferably 1500 MPa or less, for example, from the viewpoint of the performance of the material. The compressive strength is measured by a method prescribed by JIS-R1639-5.

The content of the complex oxide particles with a high content of Ni is, for example, preferably 30% by mass or more and 100% by mass or less, and more preferably 80% by mass or more and 95% by mass or less based on the total amount of the positive electrode active material. When the content of the complex oxide particles with a high content of Ni in the positive electrode active material layer is less than 30% by mass, for example, the effect of suppressing an increase in the capacity deterioration rate after the storage of the battery at high temperature may decrease as compared with when the content satisfies the above-mentioned range. The positive electrode active material may include particles of a positive electrode active material other than the complex oxide particles with a high content of Ni, examples of the particles include complex oxide particles such as $LiCoO_2$ and $LiMn_2O_4$ not including Ni, and complex oxide particles wherein the ratio of Ni to the total number of moles of the metallic elements except Li is less than 80 mol %.

The content of the positive electrode active material is, for example, preferably 70% by mass or more and 99% by mass or less, and more preferably 80% by mass or more and 95% by mass or less based on the total amount of the positive electrode mixture layer.

An example of a method for producing complex oxide particles with a high content of Ni will be described.

A method for producing complex oxide particles with a high content of Ni include: a complex hydroxide synthesis step of obtaining a Ni, Co and Al complex hydroxide, a Ni, Co and Mn complex hydroxide, or the like; a raw material mixing step of mixing the complex hydroxide and a lithium compound to obtain a raw material mixture; and a firing step of firing the raw material mixture to obtain complex oxide particles with a high content of Ni.

Examples of the complex hydroxide synthesis step include a coprecipitation method for dropping a solution of an alkali such as sodium hydroxide with stirring a solution of metal salts including Ni, Co, Al (or Mn) and the like, and adjusting the pH to the alkali side (for example, 8.5 to 11.5) to deposit (coprecipitate) a Ni, Co and Al complex hydroxide or a Ni, Co and Mn complex hydroxide. The complex hydroxide synthesis step preferably includes an aging step of maintaining the complex hydroxide in the reaction solution as it is after the precipitation of the complex hydroxide. The complex oxide particles with a high content of Ni obtained finally is easily obtained as unaggregated particles thereby.

The raw material mixing step is a method of, for example, mixing the above-mentioned complex hydroxide and a lithium compound such as lithium hydroxide, lithium carbonate or lithium nitrate to obtain a raw material mixture. To adjust the ratio of the BET specific surface area after the particle compression test (B) to the BET specific surface area before the particle compression test (A) of the complex oxide particles with a high content of Ni obtained finally (B/A) to 1.0 or more and 3.0 or less, the mixing ratio of the complex hydroxide to the lithium compound, for example, the metallic elements (Ni+Co+Al or Mn):Li, is preferably adjusted to the range of 1.0:1.02 to 1.0:1.2 by molar ratio.

The firing step is a method, for example, for firing the above-mentioned raw material mixture in an oxygen atmosphere to obtain complex oxide particles with a high content of Ni. To adjust the ratio of the BET specific surface area after the particle compression test (B) to the BET specific surface area before the particle compression test (A) of the complex oxide particles with a high content of Ni obtained finally (B/A) to 1.0 or more and 3.0 or less, the firing temperature of the raw material mixture is preferably adjusted, for example, to the range of 750° C. or more and 1100° C. or less. The firing temperature is preferably 20 hours to 150 hours, and more preferably 20 hours to 100 hours. When the firing time of complex oxide particles with a high content of Ni is more than 150 hours, for example, the material physical properties or the electrochemical characteristics may be deteriorated as compared with when the firing time is 150 hours or less.

Examples of the conductive agent included in the positive electrode active material layer include carbon powders such as carbon black, acetylene black, ketjen black and graphite. These may be used singly or in combinations of two or more.

Examples of the binding agent included in the positive electrode active material layer include fluorine-containing polymers and rubber-based polymers. Examples of the fluorine-containing polymers include polytetrafluoroethylene (PTFE), polyvinylidene fluoride (PVDF), or modified product thereof. Examples of the rubber-based polymers include an ethylene-propylene-isoprene copolymer and an ethylene-propylene-butadiene copolymer. These may be used singly or in combinations of two or more.

The positive electrode 11 of the present embodiment is obtained, for example, by forming a positive electrode active material layer on a positive electrode current collector by applying positive electrode mixture slurry including the positive electrode active material, the conductive agent, the binding agent and the like and drying the slurry, and rolling the positive electrode mixture layer.

[Negative Electrode]

The negative electrode 12 comprises, for example, a negative electrode current collector and a negative electrode active material layer formed on the negative electrode current collector. Foil of a metal such as copper which is stable in the potential range of the negative electrode, a film wherein the metal is disposed on the outer layer, or the like can be used for the negative electrode current collector. The negative electrode active material layer includes, for example, a negative electrode active material, a binding agent, a thickening agent, and the like.

The negative electrode active material is not particularly limited as long as the active material is a material which can occlude and emit lithium ions, and examples of the active material include metal lithium; lithium alloys such as a lithium-aluminum alloy, a lithium-lead alloy, a lithium-silicon alloy and a lithium-tin alloy; carbon materials such as graphite, graphite fluoride, coke and a fired organic substance; and metal oxides such as $SnO_2$, SnO and $TiO_2$. These may be used singly or in combinations of two or more.

Although, for example, a fluorine-containing polymer, a rubber-based polymer, or the like can also be used as the binding agent, as is the case with the positive electrode, a styrene-butadiene copolymer (SBR) or a modified product thereof may be used.

Examples of the thickening agent include carboxymethyl cellulose (CMC) and polyethylene oxide (PEO). These may be used singly or in combinations of two or more.

The negative electrode 12 of the present embodiment is obtained, for example, by forming a negative electrode active material layer on a negative electrode current collector by applying negative electrode mixture slurry including the negative electrode active material, the binding agent, the thickening agent and the like and drying the slurry, and rolling the negative electrode active material layer.

[Non-Aqueous Electrolyte]

The non-aqueous electrolyte includes the cyclic carboxylic anhydride, the non-aqueous solvent, and the electrolyte salt dissolved in the non-aqueous solvent. The non-aqueous electrolyte is not limited to a liquid electrolyte (non-aqueous electrolytic solution), and may be a solid electrolyte using a gel polymer or the like.

The cyclic carboxylic anhydride included in the non-aqueous electrolyte is not particularly limited as long as the cyclic carboxylic anhydride is a substance represented by the above formula (1). However, specific examples of the cyclic carboxylic anhydride include diglycolic anhydride, methyl diglycolic anhydride, dimethyl diglycolic anhydride, ethyl diglycolic anhydride, vinyl diglycolic anhydride, allyl diglycolic anhydride and divinyl diglycolic anhydride. These may be singly or in combinations of two or more. Among these, diglycolic anhydride is preferable in that an increase in the capacity deterioration rate after the storage of the battery at high temperature can be further suppressed.

The content of the cyclic carboxylic anhydride is preferably 0.1% by mass or more and 2.5% by mass or less based on the total mass of the non-aqueous electrolyte. The content of the cyclic carboxylic anhydride is preferably 0.03 parts by mass or more and 3 parts by mass or less per 100 parts by mass of the positive electrode active material. The content of the cyclic carboxylic anhydride is preferably 0.05 parts by mass or more and 5 parts by mass or less per 100 parts by mass of the negative electrode active material. When the content of the cyclic carboxylic anhydride satisfies at least one of the above, an increase in the capacity deterioration rate after the storage of the battery at high temperature may be further suppressed as compared with when the content satisfies none of the above.

The non-aqueous solvent preferably includes a fluorine-containing cyclic carbonate. A non-aqueous solvent including the fluorine-containing cyclic carbonate may suppress a decrease in the charge and discharge cycle characteristics of the non-aqueous electrolyte secondary battery as compared with a non-aqueous solvent not including the fluorine-containing cyclic carbonate. The fluorine-containing cyclic carbonate included in the non-aqueous solvent is not particularly limited as long as the carbonate is a cyclic carbonate containing at least one fluorine atom. Examples of the carbonate include monofluoroethylene carbonate (FEC), 1,2-difluoroethylene carbonate, 1,2,3-trifluoropropylene carbonate, 2,3-difluoro-2,3-butylene carbonate and 1,1,1,4,4,4-hexafluoro-2,3-butylene carbonate. These may be singly or in combinations of two or more. Among these, monofluoroethylene carbonate (FEC) is preferable from the viewpoint of suppressing the amount of hydrofluoric acid generated at high temperature, or the like.

The content of the fluorine-containing cyclic carbonate is, for example, preferably 0.1% by volume or more and 50% by volume or less based on the total volume of the non-aqueous solvent. When the content of the fluorine-containing cyclic carbonate in the non-aqueous solvent satisfies the above-mentioned range, a decrease in the charge and discharge cycle characteristics may be suppressed as compared with when the content does not satisfy the above-mentioned range.

The non-aqueous solvent may include, for example, a non-fluorine-containing solvent besides the fluorine-containing cyclic carbonate. Examples of the non-fluorine-containing solvent include cyclic carbonates; chain-like carbonates; carboxylate esters; cyclic ethers, chain-like ethers; nitriles such as acetonitrile; amides such as dimethylformamide; and mixed solvents of these.

Examples of the above-mentioned cyclic carbonates include ethylene carbonate (EC), propylene carbonate (PC) and butylene carbonate. Examples of the above-mentioned chain-like carbonates include dimethyl carbonate, methyl ethyl carbonate (EMC), diethyl carbonate, methyl propyl carbonate, ethyl propyl carbonate and methyl isopropyl carbonate. These may be singly or in combinations of two or more.

Examples of the above-mentioned carboxylate esters include methyl acetate, ethyl acetate, propyl acetate, methyl propionate (MP), ethyl propionate and γ-butyrolactone. These may be singly or in combinations of two or more.

Examples of the above-mentioned cyclic ethers include 1,3-dioxolane, 4-methyl-1,3-dioxolane, tetrahydrofuran, 2-methyltetrahydrofuran, propylene oxide, 1,2-butylene oxide, 1,3-dioxane, 1,4-dioxane, 1,3,5-trioxane, furan, 2-methylfuran, 1,8-cineol and crown ethers. These may be singly or in combinations of two or more.

Examples of the above-mentioned chain-like ethers include 1,2-dimethoxyethane, diethyl ether, dipropyl ether, diisopropyl ether, dibutyl ether, dihexyl ether, ethyl vinyl ether, butyl vinyl ether, methyl phenyl ether, ethyl phenyl ether, butyl phenyl ether, pentyl phenyl ether, methoxytoluene, and benzyl ethyl ether, diphenyl ether, dibenzyl ether, o-dimethoxybenzene, 1,2-diethoxyethane, 1, 2-dibutoxyethane, diethylene glycol dimethyl ether, diethylene glycol diethyl ether, diethylene glycol dibutyl ether, 1,1-dimethoxymethane, 1,1-diethoxyethane, triethylene glycol dimethyl ether and tetraethylene glycol dimethyl. These may be singly or in combinations of two or more.

The electrolyte salt is preferably a lithium salt. Examples of the lithium salt include $LiBF_4$, $LiClO_4$, $LiPF_6$, $LiAsF_6$, $LiSbF_6$, $LiAlCl_4$, LiSCN, $LiCF_3SO_3$, $LiCF_3CO_2$, $Li(P(C_2O_4)F_4)$, $LiPF_{6-x}(C_nF_{2n+1})_x$ wherein 1<x<6, and n is 1 or 2, $LiB_{10}Cl_{10}$, LiCl, LiBr, LiI, lithium chloroborane, lithium lower aliphatic carboxylates, borates such as $Li_2B_4O_7$ and $Li(B(C_2O_4)F_2)$, and imide salts such as $LiN(SO_2CF_3)_2$ and $LiN(C_1F_{2l+1}SO_2)(C_mF_{2m+1}SO_2)$ wherein 1 and m are integers of 0 or more. These lithium salts may be used singly or as a mixture of two or more. Among these, $LiPF_6$ are preferably used from the viewpoints of ion conductivity, electrochemical stability and the like. The concentration of the lithium salt is preferably 0.8 to 1.8 mol per 1 L of the non-aqueous solvent.

[Separator]

For example, a porous sheet or the like having ion permeability and insulation properties is used for the separator 13. Specific examples of the porous sheet include fine porous thin films, woven fabrics and nonwoven fabrics. As the material of the separator, olefin-based resins such as polyethylene and polypropylene; cellulose; and the like are preferable. The separator may be a layered body having a cellulose fiber layer and a thermoplastic resin fiber layer of an olefin-based resin or the like. The separator may be a multilayer separator including a polyethylene layer and a polypropylene layer, and a separator wherein a material such as an aramid-based resin or a ceramic is applied to the surface of the separator may be used.

EXAMPLES

Although the present disclosure will be further described by Examples hereinafter, the present disclosure is not limited to the following Examples.

Example 1

[Production of Complex Oxide Particles with High Content of Ni]

$[Ni_{0.8}Co_{0.15}Al_{0.05}](OH)_2$ obtained by a coprecipitation method and LiOH were mixed in an Ishikawa-type grinding mortar so that the molar ratio of Li to the total amount of Ni, Co and Al was 1.1:1.0. Then, this mixture was fired in an oxygen atmosphere at 780° C. for 50 hours to obtain complex oxide particles with a high content of Ni.

The obtained complex oxide particles with a high content of Ni were embedded into a resin, a section of the particles was prepared by cross section polisher (CP) processing, and this section was observed through a SEM. Consequently, the complex oxide particles with a high content of Ni existed in a state in which particles were completely separated into individual primary particles or a state in which 2 to 10 primary particles were gathered, and were unaggregated particles. When, in the positive electrode manufactured below, its section is observed through the SEM, the complex oxide particles with a high content of Ni existed in a state in which particles were completely separated into individual primary particles, or existed in a state in which 2 to 5 primary particles were gathered in the positive electrode mixture layer, and existed in a state of unaggregated particles in the positive electrode active material layer.

The BET specific surface area of the obtained complex oxide particles with a high content of Ni was measured, so that the BET specific surface area was 0.685 m²/g. A compression test was performed under the above-mentioned condition, and the BET specific surface area of the complex oxide particles with a high content of Ni after the compression test was measured, so that the BET specific surface area was 1.314 m²/g. That is, in the obtained complex oxide particles, the ratio of the BET specific surface area after the particle compression test (B) to the BET specific surface area before the particle compression test (A) (B/A) was 1.918.

The compressive strength of the obtained complex oxide particles with a high content of Ni was 600 MPa. The measuring method is as mentioned above.

[Manufacturing of Positive Electrode]

The above-mentioned complex oxide particles with a high content of Ni as a positive electrode active material, acetylene black as a conductive agent, and polyvinylidene fluoride as a binding agent were mixed so that the mass ratio was 100:1:1. N-methyl-2-pyrrolidone was then added to prepare positive electrode mixture slurry. Subsequently, this positive electrode mixture slurry was applied to both sides of the positive electrode current collector comprising aluminum foil, and this was dried and then rolled with a rolling roller to manufacture a positive electrode in which positive electrode active material layers were formed on both sides of the positive electrode current collector.

[Manufacturing of Negative Electrode]

Graphite as a negative electrode active material, a styrene-butadiene copolymer (SBR) as a binding agent, and carboxymethyl cellulose (CMC) as a thickening agent were mixed so that the mass ratio was 100:1:1, water was added to prepare negative electrode mixture slurry. Subsequently, the negative electrode mixture slurry was applied to both sides of a negative electrode current collector comprising copper foil, and this was dried and then rolled with the rolling roller to manufacture a negative electrode in which negative electrode active material layers were formed on both sides of the negative electrode current collector.

[Preparation of Non-Aqueous Electrolyte]

$LiPF_6$ was dissolved in a mixed solvent obtained by mixing monofluoroethylene carbonate (FEC), dimethyl carbonate (DMC) and ethyl methyl carbonate (EMC) so that the volume ratio was 15:45:40 so that the concentration was 1.3 mol/L. Further, 0.2% by mass diglycolic anhydride (DGA) was dissolved. A non-aqueous electrolyte was prepared. The content of diglycolic anhydride (DGA) was 0.08 parts by mass per 100 parts by mass of the positive electrode active material, and was 0.12 parts by mass per 100 parts by mass of the negative electrode active material.

[Manufacturing of Non-Aqueous Electrolyte Secondary Battery]

The above-mentioned positive electrode and negative electrode were wound through a separator to manufacture an electrode assembly, the electrode assembly was stored with the above-mentioned non-aqueous electrolyte in a bottomed cylindrical battery case, and the opening of the battery case was sealed with a gasket and a sealing assembly. This was used as the non-aqueous electrolyte secondary battery of Example 1.

Example 2

A non-aqueous electrolyte secondary battery was manufactured in the same way as in Example 1 except that the content of diglycolic anhydride (DGA) was changed into 0.4% by mass in the preparation of a non-aqueous electrolyte. The content of diglycolic anhydride (DGA) was 0.16 parts by mass per 100 parts by mass of the positive electrode active material, and was 0.25 parts by mass per 100 parts by mass of the negative electrode active material.

Example 3

A non-aqueous electrolyte secondary battery was manufactured in the same way as in Example 1 except that the content of diglycolic anhydride (DGA) was changed into 0.6% by mass in the preparation of a non-aqueous electrolyte. The content of diglycolic anhydride (DGA) was 0.23 parts by mass per 100 parts by mass of the positive electrode active material, and was 0.38 parts by mass per 100 parts by mass of the negative electrode active material.

Example 4

A non-aqueous electrolyte secondary battery was manufactured in the same way as in Example 1 except that the content of diglycolic anhydride (DGA) was changed into 0.8% by mass in the preparation of a non-aqueous electrolyte. The content of diglycolic anhydride (DGA) was 0.31 parts by mass per 100 parts by mass of the positive electrode active material, and was 0.51 parts by mass per 100 parts by mass of the negative electrode active material.

Example 5

A non-aqueous electrolyte secondary battery was manufactured in the same way as in Example 1 except that the content of diglycolic anhydride (DGA) was changed into 1.0% by mass in the preparation of a non-aqueous electrolyte. The content of diglycolic anhydride (DGA) was 0.39 parts by mass per 100 parts by mass of the positive electrode active material, and was 0.64 parts by mass per 100 parts by mass of the negative electrode active material.

Example 6

In the production of complex oxide particles with a high content of Ni, $[Ni_{0.82}Co_{0.03}Mn_{0.15}](OH)_2$ obtained by the coprecipitation method and $Li_2CO_3$ were mixed in an Ishikawa-type grinding mortar so that the molar ratio of Li to the total amount of Ni, Co and Mn was 1.1:1.0. Then, this mixture was fired in the air atmosphere at 1000° C. for 20 hours to obtain complex oxide particles with a high content of Ni. A non-aqueous electrolyte secondary battery was manufactured in the same way as in Example 1 except that this complex oxide particles with a high content of Ni was used.

The complex oxide particles with a high content of Ni obtained in Example 6 were embedded into a resin, and a section of the particles was prepared by cross section polisher (CP) processing. When this section was observed through the SEM, the particles were unaggregated particles. Also, in a section of the positive electrode, the complex oxide particles with a high content of Ni existed in the state of unaggregated particles in the positive electrode mixture layer.

The BET specific surface area of the complex oxide particles with a high content of Ni obtained in Example 6 was measured, so that the BET specific surface area was 0.456 m²/g. A compression test was performed under the above-mentioned conditions, and the BET specific surface area of the complex oxide particles with a high content of Ni after the compression test was measured, so that the BET specific surface area was 1.183 m²/g. That is, in the complex oxide particles obtained in Example 6, the ratio of the BET specific surface area after the particle compression test (B) to the BET specific surface area before the particle compression test (A) (B/A) was 2.59.

The compressive strength of the obtained complex oxide particles with a high content of Ni was 256 MPa.

Comparative Example 1

A non-aqueous electrolyte secondary battery was manufactured in the same way as in Example 1 except that diglycolic anhydride (DGA) was not added in the preparation of a non-aqueous electrolyte.

Comparative Example 2

Complex oxide particles with a high content of Ni were manufactured in the same way as in Example 1 except that the molar ratio of Li to the total amount of Ni, Co and Al was changed into 1.3:1.0, the firing temperature was changed into 730° C. in the production of the complex oxide particles with a high content of Ni. A non-aqueous electrolyte secondary battery was manufactured in the same way as in Example 1 except that the complex oxide particles with a high content of Ni obtained in Comparative Example 2 was used, and diglycolic anhydride (DGA) was not added in the preparation of a non-aqueous electrolyte.

The complex oxide particles with a high content of Ni obtained in Comparative Example 2 were embedded into a resin, a section of the particles was prepared by cross section polisher (CP) processing, and this section was observed through the SEM. Consequently, the complex oxide particles with a high content of Ni obtained in Comparative Example 2 were aggregated particles wherein hundreds of primary particles or more were gathered. Also, in a section of the positive electrode, the complex oxide particles with a high content of Ni existed in the state of aggregated particles wherein hundreds of primary particles or more were gathered in the positive electrode mixture layer.

The BET specific surface area of the complex oxide particles with a high content of Ni obtained in Comparative Example 2 was measured, so that the BET specific surface area was 0.368 m²/g. A compression test was performed under the above-mentioned conditions, and the BET specific surface area of the complex oxide particles with a high content of Ni after the compression test was measured, so that the BET specific surface area was 2.529 m²/g. That is, in the complex oxide particles obtained in Comparative Example 2, the ratio of the BET specific surface area after the particle compression test (B) to the BET specific surface area before the particle compression test (A) (B/A) was 6.87.

The compressive strength of the complex oxide particles with a high content of Ni obtained in Comparative Example 2 was 132 MPa.

Comparative Example 3

A non-aqueous electrolyte secondary battery was manufactured in the same way as in Example 1 except that the complex oxide particles with a high content of Ni obtained in Comparative Example 2 were used.

Comparative Example 4

A non-aqueous electrolyte secondary battery was manufactured in the same way as in Example 1 except that the complex oxide particles with a high content of Ni obtained in Comparative Example 2 were used, and the content of diglycolic anhydride (DGA) was changed into 0.4% by mass in the preparation of a non-aqueous electrolyte.

Comparative Example 5

A non-aqueous electrolyte secondary battery was manufactured in the same way as in Example 1 except that the complex oxide particles with a high content of Ni obtained in Comparative Example 2 were used, and the content of diglycolic anhydride (DGA) was changed into 0.6% by mass in the preparation of a non-aqueous electrolyte.

Comparative Example 6

A non-aqueous electrolyte secondary battery was manufactured in the same way as in Example 1 except that the complex oxide particles with a high content of Ni obtained in Comparative Example 2 were used, and the content of diglycolic anhydride (DGA) was changed into 0.8% by mass in the preparation of a non-aqueous electrolyte.

Comparative Example 7

A non-aqueous electrolyte secondary battery was manufactured in the same way as in Example 1 except that the complex oxide particles with a high content of Ni obtained in Comparative Example 2 were used, and the content of diglycolic anhydride (DGA) was changed into 1.0% by mass in the preparation of a non-aqueous electrolyte.

[Measurement of Capacity Deterioration Rate after Storage at High Temperature]

As to each of the non-aqueous electrolyte secondary batteries of the Examples and the Comparative Examples, the capacity deterioration rate after storage at high temperature was measured under the following conditions. At an environmental temperature of 25° C., the battery was charged at a constant current of 0.5 C until the voltage was 4.1 V, the battery was then subjected to constant voltage charge at 4.1 V until the current value was 0.05 C, and the charge was completed (the charge is called charge A). After a 10-minute pause, the battery was subjected to constant current discharge at a constant current of 0.5 C until the voltage was 3.0 V (the discharge is called discharge A), and the discharge capacity at that time was defined as an initial capacity. After a 10-minute pause, the battery was subjected to the above-mentioned charge A and then stored at an environmental temperature of 60° C. for 5 days. After the storage, the temperature was lowered to room temperature, the battery was then subjected to only the above-mentioned discharge A. After a 10-minute pause, the battery was subjected to the above-mentioned charge A. After a 10-minute pause, the battery was subjected to the above-mentioned discharge A. The discharge capacity at that time was defined as a capacity after storage. The capacity deterioration rate after storage at high temperature was calculated by the following expression.

Capacity deterioration rate after storage at high temperature (%)=(initial capacity−capacity after storage)/initial capacity×100

Table 1 shows the result of the capacity deterioration rate after storage at high temperature in each of the non-aqueous electrolyte secondary batteries of the Examples and the Comparative Examples.

TABLE 1

|  | Positive electrode active material | | | Non-aqueous electrolyte | Battery characteristic Capacity deterioration rate after storage at high temperature (%) |
| --- | --- | --- | --- | --- | --- |
|  | Constituent element | Aggregated/ unaggregated | Ratio B/A | DGA content (% by mass) | |
| Example 1 | Li, Ni, Co, Al | Unaggregated | 1.918 | 0.2 | 4.4 |
| Example 2 | Li, Ni, Co, Al | Unaggregated | 1.918 | 0.4 | 4.4 |
| Example 3 | Li, Ni, Co, Al | Unaggregated | 1.918 | 0.6 | 4.3 |
| Example 4 | Li, Ni, Co, Al | Unaggregated | 1.918 | 0.8 | 4.4 |
| Example 5 | Li, Ni, Co, Al | Unaggregated | 1.918 | 1.0 | 4.3 |
| Example 6 | Li, Ni, Co, Mn | Unaggregated | 2.59 | 0.2 | 4.6 |
| Comparative Example 1 | Li, Ni, Co, Al | Unaggregated | 1.918 | 0 | 5.9 |
| Comparative Example 2 | Li, Ni, Co, Al | Aggregated | 6.87 | 0 | 5.3 |
| Comparative Example 3 | Li, Ni, Co, Al | Aggregated | 6.87 | 0.2 | 5.4 |
| Comparative Example 4 | Li, Ni, Co, Al | Aggregated | 6.87 | 0.4 | 5.3 |
| Comparative Example 5 | Li, Ni, Co, Al | Aggregated | 6.87 | 0.6 | 5.3 |
| Comparative Example 6 | Li, Ni, Co, Al | Aggregated | 6.87 | 0.8 | 5.2 |
| Comparative Example 7 | Li, Ni, Co, Al | Aggregated | 6.87 | 1.0 | 5.2 |

In any of the Examples and the Comparative Examples, a positive electrode active material including complex oxide particles, including Ni, Co and Li and including at least either of Mn and Al, wherein the ratio of Ni to the total number of moles of the metallic elements except Li is 80 mol % or more is used. However, in the above-mentioned complex oxide particles, the capacity deterioration rate after storage at high temperature of each of Examples 1 to 6, wherein the ratio of the BET specific surface area after a particle compression test (B) to the BET specific surface area before the particle compression test (A) (B/A) was 1.0 or more and 3.0 or less, and a non-aqueous electrolyte including a cyclic carboxylic anhydride represented by the above formula (1) was used, exhibits a low value as compared with Comparative Examples 1 to 7, wherein the ratio B/A did not satisfy the above-mentioned range, or a non-aqueous electrolyte including a cyclic carboxylic anhydride represented by the above formula (1) was not used. An increase in the capacity deterioration rate was suppressed.

Example 7

A non-aqueous electrolyte secondary battery was manufactured in the same way as in Example 1 except that the content of diglycolic anhydride (DGA) was changed into 0.1% by mass in the preparation of a non-aqueous electrolyte.

The initial capacity of each of the non-aqueous electrolyte secondary batteries of Examples 1 to 7 and Comparative Example 1 was measured under the following conditions. At an environmental temperature of 25° C., the battery was charged at a constant current of 0.5 C until the voltage was 4.1 V, the battery was subjected to constant voltage charge at 4.1 V until the current value was 0.05 C, and the charge was completed. After a 10-minute pause, the battery was subjected to constant current discharge at a constant current of 0.5 C until the voltage was 3.0 V. The discharge capacity at that time was defined as an initial capacity.

Table 2 shows the initial capacity ratio of each of the non-aqueous electrolyte secondary batteries of Examples 1 to 5 and 7 and Comparative Example 1. The initial capacity ratios are values relatively showing the initial capacities of Examples 1 to 5 and 7 with the initial capacity of Comparative Example 1 defined as a standard (100%).

TABLE 2

|  | Non-aqueous electrolyte DGA content (% by mass) | Battery characteristics Initial capacity ratio (%) |
|---|---|---|
| Example 1 | 0.2 | 100.8 |
| Example 2 | 0.4 | 100.8 |
| Example 3 | 0.6 | 100.5 |
| Example 4 | 0.8 | 100.2 |
| Example 5 | 1.0 | 100.2 |
| Example 7 | 0.1 | 100.6 |
| Comparative Example 1 | 0 | 100.0 |

As shown in Table 2, the initial capacity of each of the non-aqueous electrolyte secondary batteries of Examples 1 to 5 and 7, wherein the non-aqueous electrolyte including the cyclic carboxylic anhydride represented by the above formula (1) was used, improved as compared with Comparative Example 1, wherein the non-aqueous electrolyte including the cyclic carboxylic anhydride represented by the above formula (1) was not used. Among Examples 1 to 5 and 7, Examples 1 and 2, wherein the contents of the cyclic carboxylic anhydride represented by the above formula (1) were 0.2% by mass or more 0.4% by mass or less based on the total mass of the non-aqueous electrolyte, exhibit the highest initial capacity.

REFERENCE SIGNS LIST 10 non-aqueous electrolyte secondary battery
11 positive electrode
12 negative electrode
13 separator
14 electrode assembly
15 case body
16 sealing assembly
17,18 insulating plates
19 positive electrode lead
20 negative electrode lead
21 projecting portion
22 filter
22a opening of filter
23 lower vent member
24 insulating member
25 upper vent member
26 cap
26a cap opening
27 gasket

The invention claimed is:

1. A non-aqueous electrolyte secondary battery, comprising:
a positive electrode;
a negative electrode; and
a non-aqueous electrolyte, wherein
the positive electrode has a positive electrode active material including complex oxide particles, including Ni, Co and Li and including at least Mn, wherein a ratio of Ni to a total number of moles of metallic elements except Li is 80 mol % or more,
the complex oxide particles exist in a state of at least one of: completely separated individual primary particles and about 2 to 15 primary particles in the positive electrode active material,
the complex oxide particles have a ratio of a BET specific surface area after a particle compression test (B) to a BET specific surface area before the particle compression test (A) (B/A) of 1.918 or more and 3.0 or less, and
the non-aqueous electrolyte includes a cyclic carboxylic anhydride represented by the following formula (1) and a non-aqueous solvent:

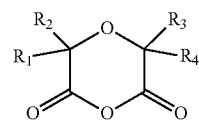

[Formula 1]

wherein $R_1$ to $R_4$ each independently represent H, an alkyl group, an alkene group or an aryl group.

2. The non-aqueous electrolyte secondary battery according to claim 1, wherein
the complex oxide particles have a compressive strength of 250 MPa or more.

3. The non-aqueous electrolyte secondary battery according to claim 1, wherein
the cyclic carboxylic anhydride includes diglycolic anhydride.

4. The non-aqueous electrolyte secondary battery according to claim 1, wherein
the non-aqueous solvent includes a fluorine-containing cyclic carbonate, and a content of the fluorine-containing cyclic carbonate is 0.1% by volume or more and 50% by volume or less based on a total volume of the non-aqueous solvent.

5. The non-aqueous electrolyte secondary battery according to claim 1, wherein
a content of the cyclic carboxylic anhydride is 0.1% by mass or more and 2.5% by mass or less based on a total mass of the non-aqueous electrolyte.

6. The non-aqueous electrolyte secondary battery according to claim 1, wherein
the content of the cyclic carboxylic anhydride is 0.03 parts by mass or more and 3 parts by mass or less per 100 parts by mass of the positive electrode active material.

7. The non-aqueous electrolyte secondary battery according to claim 1, wherein
the negative electrode includes a negative electrode active material, and
a content of the cyclic carboxylic anhydride is 0.05 parts by mass or more and 5 parts by mass or less per 100 parts by mass of the negative electrode active material.

8. The non-aqueous electrolyte secondary battery according to claim 1, wherein the complex oxide particles further include Al.

* * * * *